United States Patent [19]

Degen et al.

[11] 3,980,520

[45] Sept. 14, 1976

[54] PROCESS FOR THE PRODUCTION OF L-MALIC ACID BY MICROBIOLOGICAL FERMENTATION AND MEANS SUITABLE FOR CARRYING OUT THE SAME

[75] Inventors: Ludwig Degen; Nicola Oddo, both of Rome; Roberto Olivieri, Mentana, all of Italy

[73] Assignee: Snam Progetti S.p.A., San Donato Milanese, Italy

[22] Filed: Dec. 21, 1973

[21] Appl. No.: 427,340

[30] Foreign Application Priority Data

Dec. 27, 1972 Italy ................................. 33567/72

[52] U.S. Cl. ................................................. 195/30
[51] Int. Cl.² ........................................... C12D 1/02
[58] Field of Search .................................... 195/30

[56] References Cited

UNITED STATES PATENTS 2,972,566  2/1961  Kitahara .............................. 195/30

Primary Examiner—Alvin E. Tanenholtz
Attorney, Agent, or Firm—Ralph M. Watson

[57] ABSTRACT

L-malic acid is prepared from fumaric acid through a microbiological fermentation process employing a microbial strain of the Paracolobactrum genus having the number 743, 745 or 746.

5 Claims, No Drawings

PROCESS FOR THE PRODUCTION OF l-MALIC ACID BY MICROBIOLOGICAL FERMENTATION AND MEANS SUITABLE FOR CARRYING OUT THE SAME

The present invention relates to a process for the production of L-malic acid, starting from fumaric acid, by microbiological fermentation and also to the means suitable for carrying out the process itself. It is known that L-malic acid may be obtained by the reaction

$$\text{fumarate} + H_2O \rightarrow \text{L-malate}$$

which is catalyzed by enzyme fumarase (fumarate hydratase or l-malate hydro-lyase); the reaction may proceed in both directions so that it is possible to produce both fumaric acid from L-malic acid and L-malic acid from fumaric acid.

Generally fumarase is extracted from pig heart and many microorganisms of various kinds such as Corynebacterium, Microbacterium, Proteus, Escherichia, Micrococcus, Bacillus, Lactobacillus, Pseudomonas, Candida, Aspergillus and Saccharomyces.

L-malic acid, obtained in such a way, must be then subjected to novel purification processes in order to obtain a product having the degree of a purity necessary for the use thereof.

It has now been found, which is a first subject of the present invention, that it is possible to obtain L-malic acid of high purity, without any purification treatment, through a fermentation process by merely using microbial strains which have not yet been used as fumarase source, belonging to Paracolobactrum genus and, as such, constituting a second subject of the present invention.

The cells recovered at the end of fermentation may be used as such for performing the enzymatic reaction: therefore a third subject of the present invention is constituted by a process for the production of fumarase starting from microbial strains of Paracolobactrum genus.

These strains, isolated from agricultural ground samples, are marked by the number 743 (CBS 405.73) and have the characteristics reported hereinafter: they have been deposited at Central Bureau Voor Schimmelcultures—Baarn-Holland.

Microscopic morphology

Single little sticks, 0.5–0.8 × 1.0–2.0 micron, without any capsule and spore, not mobile, Gram-negative.

Macroscopic Morphology

Colonies on nourishing agar (Difco): thick, white, entire, moist, mucous.

Culture on a nourishing medium (Difco): cloudy, with pellicle and plentiful deposit.

Slant of nourishing agar (Difco): plentiful, confluent, white, moist, metallic brightness.

Infusion in nourishing gelatin (Difco): thick, white, moist, confluent to surface, without liquefaction.

Biochemical characteristics:

Acid and gas from glucose, fructose, galactose, arabinose, maltose, mannitol, starch.
Lactose not fermented within 30 days.
Citrate utilized as carbon source.
Methyl red test: negative.
Voges-Proskauer test: positive.
Indole: negative.
$H_2S$: negative.
Nitrites produced by nitrates.
Catalysis: positive.
Litmus milk: acidification with coagulation, no peptonization.

Growth conditions: it grows well on laboratory media. The optimum temperature is about at 25°C, aerobe (facultative anaerobe).

By comparing the aforesaid characteristics with the descriptions of "Bergey's Manual of Determinative Bacteriology" the 8th Edition, the inventive strains belong to Family: Enterobacteriaceae
Tribe: Escherichdeae
Genus: Paracolobactrum
Species: Paracolobactrum aerogenoides According to the present invention, L-malic acid is produced through a fermentation process by using one of the aforesaid bacterial strains and, as culture medium, a salt solution containing nitrogen and carbon sources in the presence of fumarate.

The microorganisms can be cultivated under aerobic conditions in culture media containing sources of carbon, nitrogen and mineral salts at a temperature ranging from 20° to 40°C, preferably from 28° to 30°C, for a period of from 18 to 36 hours, preferably 24 hours, and at pH of from 5.5 to 8, preferably 7.

As carbon source use may be made of glucose, starch, glycerol and molasses. The substrate (fumaric acid) is added at concentrations of 1 to 10% or 1 to 5% before adjusting pH with sodium hydroxide.

As nitrogen source use may be made of peptone, hydrolized derivatives of casein or soja, ammonium or sodium nitrates, ammonium sulphate or phosphate, corn steep liquor (CSL), malt extract etc.

The yield as l-malic acid is increased when the aeration is reduced. As noted above the cells are recovered at the end of fermentation and may be used as such in the enzymatic reaction.

When used is made of the bacterial cells in the enzymatic conversion of fumarate into malate they are cultivated in media similar to the ones of the fermentative process.

As carbon source use may be made of glucose, starch, glycerol, molasses, fumarate, tartrate, citrate or acetate in concentrations from 1 to 5%. Otherwise use may be made also of extracts of these cells.

In such a case the cells are broken according to one of the known methods and use is made of the raw extract or the partially purified one containing enzyme.

The enzyme dosage may be carried out according to the methods reported in the literature. One unity corresponds to the enzyme amount which, in 1 minute at the temperature of 25°C, let O.D. change of 0.001. Malic acid is dosed in a spectrometry way, according to a method described in Modern Food Analysis (Hart-Fisher 1971), with sulphuric acid and 2–7 naphtalendiole (O.D. = optical density).

The proteins are determined in a spectrophotometric way by means of a differential reading at 224 and 233 nm against a standard curve constituted by known concentrations of albumin. The specific activity is expressed as unities/mg of proteins (nm = nanometer).

From what has been said above further working characteristics may be more clearly understood by examining the following examples, hereinafter reported in order to better illustrate the invention without limiting the purposes thereof.

EXAMPLE 1

A culture medium was prepared having the following composition:

| | | |
|---|---|---|
| fumaric acid | 20 | g/l |
| glucose | 20 | g/l |
| yeast extract | 1 | g/l |
| NaNO₃ | 5 | g/l |
| K₂HPO₄ | 2 | g/l |
| MgSO₄ . 7H₂O | 0.5 | g/l |
| Tween 80 | 1 | g/l |

The aforesaid products were dissolved in demineralized water brought to a pH of 7 by sodium hydroxide. It was sterilized for 20 minutes at 110°C. The medium was put into 500 ml flasks having a broad neck, by adding 100 ml of medium to each flask. They were inoculated by a suspension of strain 743 grown for 24 hours at 30°C on slants of nourishing agar. The optical density of the bacterial suspension used as inoculant, diluted 1/10, was 0.200 at 550 nm.

The incubation was carried out under an orbital stirring at 3°C for 88 hours.

4.5 g/l fumaric acid remained in the fermentation medium and 17.25 g/l of L-malic acid were formed corresponding to a 75% yield.

EXAMPLE 2

Use was made of 20 liters capacity laboratory fermentation apparatus equipped with four antisloshing buffles and a turbine having eight blades, containing 17 liters of the following medium:

| | | |
|---|---|---|
| fumaric acid | 20 | g/l |
| yeast extract | 1 | g/l |
| NaNO₃ | 5 | g/l |
| K₂HPO₄ | 2 | g/l |
| MgSO₄ . 7H₂O | 0.5 | g/l | in demineralized water, brought to a pH of 7 by sodium hydroxide and sterilized at 110°C for 20 minutes; therein were inoculated 340 ml (=2%) of a culture of 24 h at 30°C of the strain 743.

The optical density of the preculture, diluted 1/10, at 550 nm was 0.200. The fermentation was carried out at 30°C for 23 hours at an aeration of 0.1 vol/vol/min. Under such conditions 10 g were obtained of moist cells per culture liter.

15 g of the obtained cells were suspended in 100 ml of 0.01 M phosphate buffer, pH of 7.0, containing 0.05 mole of fumaric acid (neutralized by sodium hydroxide). The mixture was stirred at 20°C. After 5 hours 1.76 g of fumaric acid and 2.6 g of L-malic acid were dosed corresponding to a 39% yield.

EXAMPLE 3

15 g of cells obtained according to example 2 were suspended into 50 ml of 0.01 M phosphate buffer, pH of 7.0. 250 ml of acetone were cold added to this suspension. The precipitate was recovered by filtration and dried under vacuum (15 mmHg, room temperature, 18 hours). 15 g of moist cells produced 2.5 g of dry cells.

2.5 g of dry cells were suspended in 100 ml of 0.01 M phosphate buffer, pH of 7.0, containing 0.05 mole of fumaric acid (neutralized by sodium hydroxide). The reaction mixture was stirred at 20°C.

After 4 hours, 1.58 g of fumaric acid remained and 4.9 g of L-malic acid were formed corresponding to a 73.2% yield.

The cells were recovered from the reaction mixture by centrifugation and again suspended in 100 ml of buffer together with fumaric acid as abovesaid. After 6 hours at 20°C, 1.58 g of fumaric acid remained and 4.9 g of L-malic acid were formed corresponding to a 73.2% yield.

EXAMPLE 4

1.5 g of cells obtained according to example 2 were suspended in 2 ml of phosphate buffer, pH of 7.0, and subjected to ultrasonic waves for 7 minutes (MSE, 7 micron). 2 ml of the over-floating were drawn after centrifugation, containing 92 mg of proteins.

These 2 ml were added to 100 ml of phosphate buffer, pH of 7.0, containing 0.05 mole of fumaric acid (neutralized by sodium hydroxide). The reaction mixture was stirred at 20°C. After 11 hours, 1.39 g of fumaric acid remained and 5.05 g of L-malic acid were formed corresponding to a 76% yield.

EXAMPLE 5

500 ml broad necked flasks, containing 100 ml of the basis culture added with the various carbon sources (glucose, sodium fumarate, tartrate, citrate and acetate) at 10 g/l concentrations, were inoculated by 1 ml of a suspension of the strain 743 and incubated for 24 hours at 30°C under an orbital stirring.

The cells were then subjected to ultrasonic waves at a temperature lower than 10°C for 7 minutes.

The dosages of the enzymatic activity were carried out with the raw extract (overfloating of the previously obtained product) at 20°C.

The moist weight of the cultures, the formed unities of enzyme and the specific activity are reported in the following table:

| Carbon source | moist weight per 100 ml of culture medium | unity per 100 ml of culture medium | specific activity unity/mg protein |
|---|---|---|---|
| glucose | 1.2 g | 13,000 | 300 |
| sodium fumarate | 1.2 g | 32,000 | 445 |
| sodium tartrate | 1.0 g | 25,000 | 405 |
| sodium citrate | 0.65 g | 10,000 | 228 |
| sodium acetate | 0.35 g | 12,000 | 382 |

What we claim is:

1. A process for the production of L-malic acid which comprises inoculating a culture with the organism Paracolobactrum aerogenoides, said culture comprising a salt solution that contains a fumarate, a nitrogen source and a carbon source, and fermenting said culture under aerobic conditions at a temperature ranging from 20° to 40°C for a period of 18 to 36 hours at a pH of 5.5 to 8, and thereafter recovering said L-malic acid.

2. Process for the production of L-malic acid according to claim 1 characterized in that the carbon sources are constituted by glucose, starch, glycerol and molasses.

3. Process for the production of L-malic acid according to claim 1 characterized in that the nitrogen source is selected among peptone, hydrolyzed derivatives of casein and soja, ammonium or sodium nitrates, ammonium sulphate or phosphate, corn steep liquor and malt extract.

4. Process for the production of L-malic acid according to claim 1 characterized in that the fermentation is carried out for a time ranging from 18 to 36 hours and at pH of from 5.5 to 8.

5. Process for the production of L-malic acid according to claim 1 characterized in that the fermentation is carried out at temperature ranging from 20° to 40°C, in a culture medium containing glucose an main carbon source and from 1–10% fumaric acid.

* * * * *